(12) United States Patent
Liang (10) Patent No.: US 10,850,281 B2
(45) Date of Patent: *Dec. 1, 2020

(54) NUCLEIC ACID ANALYSIS APPARATUS (71) Applicant: Delta Electronics Int'l (Singapore) Pte Ltd, Singapore (SG)

(72) Inventor: Qian Liang, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 323 days.

This patent is subject to a terminal disclaimer.

(21) Appl. No.: 15/938,082

(22) Filed: Mar. 28, 2018

(65) Prior Publication Data

US 2018/0214877 A1 Aug. 2, 2018

Related U.S. Application Data

(63) Continuation-in-part of application No. 15/700,791, filed on Sep. 11, 2017, now Pat. No. 10,654,038.

(Continued)

(30) Foreign Application Priority Data

Feb. 8, 2018 (SG) .......................... 10201801085V (51) Int. Cl.
*B01L 7/04* (2010.01)
*C12Q 1/6844* (2018.01)
(Continued)

(52) U.S. Cl.
CPC ............ *B01L 7/04* (2013.01); *C12N 15/1003* (2013.01); *C12Q 1/6844* (2013.01); *G01N 35/00* (2013.01);
(Continued)

(58) Field of Classification Search
CPC ....... C12Q 1/6844; B01L 7/5255; B01L 7/04; B01L 2200/025; B01L 2200/14;
(Continued)

(56) References Cited

U.S. PATENT DOCUMENTS 8,441,629 B2 5/2013 Kolesnychenko et al.
2005/0233324 A1 10/2005 Corbett et al.
(Continued)

FOREIGN PATENT DOCUMENTS

CN 101675170 A 3/2010
CN 102341710 A 2/2012
(Continued)

*Primary Examiner* — Gautam Prakash
(74) *Attorney, Agent, or Firm* — Kirton McConkie; Evan R. Witt (57) ABSTRACT

A nucleic acid analysis apparatus with isothermal based amplification includes a chamber, a fluid delivery unit, a thermal unit, a rotational driven unit and at least one optical unit. The chamber includes a cartridge mounted therein. The fluid delivery unit is connected with the chamber and adapted to transport reagents within the cartridge for sample purification and/or nucleic acid extraction. The thermal unit is disposed in the chamber and adapted to provide a predefined temperature for nucleic acid amplification. The rotational driven unit is connected with the chamber and comprises a motion control unit, wherein the motion control unit is capable of pressing the cartridge during sample purification and/or nucleic acid extraction and rotating the cartridge with a predefined program during nucleic acid amplification and/or detection. The at least one optical unit is disposed on the chamber and includes plural optical components for detection.

18 Claims, 12 Drawing Sheets

Related U.S. Application Data (60) Provisional application No. 62/393,211, filed on Sep. 12, 2017, provisional application No. 62/393,223, filed on Sep. 12, 2017.

(51) Int. Cl.
*G01N 35/00* (2006.01)
*C12N 15/10* (2006.01)

(52) U.S. Cl.
CPC ... *B01L 2200/025* (2013.01); *B01L 2200/026* (2013.01); *B01L 2200/14* (2013.01); *B01L 2200/16* (2013.01); *B01L 2300/0654* (2013.01); *B01L 2300/1883* (2013.01); *G01N 2035/00356* (2013.01)

(58) Field of Classification Search
CPC ....... B01L 2200/026; B01L 2300/1805; B01L 2300/0663; B01L 2300/0654; B01L 2200/16; B01L 2300/1883; C12N 15/1003; G01N 35/00; G01N 2035/00356
See application file for complete search history.

(56) References Cited

U.S. PATENT DOCUMENTS

| | | |
|---|---|---|
| 2006/0040303 A1 | 2/2006 | Weilke |
| 2006/0204997 A1 | 9/2006 | Macioszek et al. |
| 2006/0223061 A1 | 10/2006 | Corbett et al. |
| 2008/0153078 A1 | 6/2008 | Braman et al. |
| 2010/0086990 A1 | 4/2010 | Stanley et al. |
| 2011/0044865 A1 | 2/2011 | Groisman et al. |
| 2014/0004621 A1* | 1/2014 | Dority et al. ..... B01L 3/502738 436/178 |
| 2015/0135502 A1* | 5/2015 | Rankin et al. ......... B41J 2/1752 29/426.2 |

FOREIGN PATENT DOCUMENTS

| | | |
|---|---|---|
| CN | 102422143 A | 4/2012 |
| CN | 104204229 A | 12/2014 |
| CN | 104630373 A | 5/2015 |
| CN | 204625604 U | 9/2015 |
| CN | 105940094 A | 9/2016 |
| CN | 106222069 A | 12/2016 |
| TW | M445583 | 1/2013 |
| TW | 201617454 A | 5/2016 |
| WO | 98/49340 A1 | 11/1998 |

* cited by examiner

NUCLEIC ACID ANALYSIS APPARATUS

CROSS-REFERENCE TO RELATED APPLICATION

This application is a continuation-in-part of U.S. patent application Ser. No. 15/700,791 filed on Sep. 11, 2017 and issued as U.S. Pat. No. 10,654,038 on May 19, 2020, which claims the benefit of U.S. Provisional Application Ser. No. 62/393,211 filed on Sep. 12, 2016 and the benefit of U.S. Provisional Application Ser. No. 62/393,223 filed on Sep. 12, 2016, the entirety of which is hereby incorporated by reference. This application also claims the priority to Singapore Patent Application No. 10201801085V filed on Feb. 8, 2018, the entirety of which is hereby incorporated by reference.

FIELD OF THE INVENTION

The present invention relates to a nucleic acid analysis apparatus, and more particularly to a nucleic acid analysis apparatus with isothermal based amplification.

BACKGROUND OF THE INVENTION

Point-of-care (POC) testing is an analytical method conducted outside the central hospital and/or laboratory using devices that can instantly interpret the results. With the increasing threat of accelerated epidemic-to-pandemic transitions of new or reemerging infectious disease outbreaks owing to globalization, decentralizing diagnostic testing at frontline clinical settings could facilitate earlier implementations of public health responses to contain and mitigate such events. In the developing countries where high infectious disease burden is compounded by diagnostic challenges due to poor clinical laboratory infrastructure and cost constraints, the potential utility for POC testing is even greater.

Although microbial culture, microscopy examination and metabolites biochemical test are still used in some scenarios, today the majority of POC device and assay development are different types of PCR (polymerase chain reaction, such as nested PCR, real-time PCR and digital PCR) based methods. PCR is an enzyme-driven process for amplifying short regions of DNA in vitro where millions of DNA copies are created by cycling among different temperatures to allow repeating steps (denaturation, annealing and elongation) of DNA replication to take place. Despite the simplicity and amplification power of PCR chemistry, requirement of precision thermal cycling among two or three temperature zones during the reaction is an inevitable drawback for PCR development in POC diagnostics.

Above mentioned limitations of the PCR reaction stimulates the development of alternative isothermal amplification methods. Instead of using thermal cycling, isothermal amplification relies on proteins that use in vivo mechanisms of DNA/RNA synthesis and dominated by enzyme activity. Therefore, miniaturize isothermal system has advantages of simple design and extremely low energy consumption. Today, various isothermal based amplification methods in terms of assay complexity (multiple enzymes or primers), acceptable detection sensitivity, and specificity have been developed, including nucleic acid sequence-based amplification (NASBA), strand displacement amplification (SDA), helicase-dependent amplification (HDA), loop-mediated isothermal amplification (LAMP), recombinase polymerase amplification (RPA) and nicking enzyme amplification reaction (NEAR).

As a relative new solution, the platform design of isothermal method lags behind its biochemical technique development. Because isothermal amplification bears higher tolerance on the sample purity, most of commercial isothermal platforms focus on creating a stable temperature environment and detection methods with middle and high throughput. The sample preparation, however, is carried out either using external equipment or manual operation. On the other hand, with the increasingly demand of simultaneously detection of multi targets, the ability of multiplexing is inevitable for isothermal based POC platforms. Unfortunately, there is no all-in-one commercial platform capable of detecting multiple targets with isothermal amplification methods.

Thus, there is a need of providing an all-in-one nucleic acid analysis apparatus with isothermal based amplification to overcome the drawbacks of the prior arts.

SUMMARY OF THE INVENTION

An object of the embodiment of the present invention is to provide an all-in-one nucleic acid analysis apparatus with isothermal based amplification, so that the processes of sample purification, nucleic acid extraction, nucleic acid amplification and nucleic acid detection may be performed on the all-in-one apparatus to realize nucleic acid analysis in real time.

Another object of the embodiment of the present invention is to provide a nucleic acid analysis apparatus capable of simultaneously detecting multiple targets with isothermal based amplification.

An additional object of the embodiment of the present invention is to provide a nucleic acid analysis apparatus with simplified structural design, improved heating efficiency and smooth fluid processing.

According to an aspect of the embodiment of the present invention, there is provided a nucleic acid analysis apparatus with isothermal based amplification, including a chamber, a fluid delivery unit, a thermal unit, a rotational driven unit, and at least one optical unit. The chamber includes a cartridge mounted therein. The fluid delivery unit is connected with the chamber and adapted to transport reagents within the cartridge for sample purification and/or nucleic acid extraction. The thermal unit is disposed in the chamber and adapted to provide a predefined temperature for nucleic acid amplification. The rotational driven unit is connected with the chamber and includes a motion control unit, wherein the motion control unit is capable of pressing the cartridge during sample purification and/or nucleic acid extraction and rotating the cartridge with a predefined program during nucleic acid amplification and/or detection. The at least one optical unit is disposed on the chamber and includes plural optical components for detection.

In an embodiment of the present invention, the chamber is able to be opened and includes a top chamber and a bottom chamber.

In an embodiment of the present invention, the cartridge is mounted in a cavity of the bottom chamber.

In an embodiment of the present invention, the motion control unit is mounted on a driven shaft of the rotational driven unit.

In an embodiment of the present invention, the motion control unit includes a sliding shell, and a rotation of the driven shaft drives the sliding shell to move downwardly and push the cartridge in tight contact with the fluid delivery unit.

In an embodiment of the present invention, the motion control unit includes at least one clamping component protruded out of a bottom surface of the sliding shell, the cartridge includes at least one trench and at least one recess structure matching the clamping component at one end of the trench, and when the sliding shell moves downwardly, the clamping component coworks with the recess structure so as to clamp the cartridge.

In an embodiment of the present invention, a reverse rotation of the driven shaft drives the sliding shell to move upwardly and lift the cartridge away from the fluid delivery unit.

In an embodiment of the present invention, the motion control unit includes a fixed part and at least one protrusion, the fixed part is mounted on the driven shaft at a fixed position, and the protrusion is protruded out of the fixed part and inserted into a groove on the sliding shell.

In an embodiment of the present invention, the motion control unit includes a spring disposed between the fixed part and the sliding shell.

In an embodiment of the present invention, the cartridge includes a reaction chip and a cartridge body, and the reaction chip is disposed on one side of the cartridge body.

In an embodiment of the present invention, the reaction chip is a planar fluidic chip and includes plural detection wells and at least one microchannel connected with the detection wells.

In an embodiment of the present invention, each of the detection wells has at least one planar surface.

In an embodiment of the present invention, the shape of the reaction chip is substantially a regular polygon.

In an embodiment of the present invention, the chamber further includes at least one positioning component, and the reaction chip includes at least one alignment slot capable of being aligned with the at least one positioning component on the chamber.

In an embodiment of the present invention, the cartridge body includes plural chambers used to store reagents for sample purification and nucleic acid extraction.

In an embodiment of the present invention, the reaction chip further includes at least one sample loading hole at a top surface of the reaction chip for adding sample.

In an embodiment of the present invention, the thermal unit surrounds the cartridge body and carries the reaction chip thereon to provide contact heating.

In an embodiment of the present invention, the rotational driven unit includes a step motor to rotate the cartridge at a predefined angle.

In an embodiment of the present invention, the optical unit includes a light source and an optical detector.

In an embodiment of the present invention, the nucleic acid analysis apparatus includes multiple optical units, and each optical unit offers a unique wavelength of illumination to detect multiple targets.

The above objects and advantages of the embodiments of the present invention become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of the embodiments of this invention are presented herein for purpose of illustration and description only; it is not intended to be exhaustive or to be limited to the precise form disclosed.

The embodiment of the present invention provides a nucleic acid analysis apparatus with isothermal based amplification. More particularly, the embodiment of the present invention provides an all-in-one nucleic acid analysis apparatus with isothermal based amplification, which integrates a fluid delivery unit, a thermal unit, a rotational driven unit, and an optical unit on one single device, so that the processes of sample purification, nucleic acid extraction, nucleic acid amplification and nucleic acid detection can be performed on the all-in-one apparatus to realize nucleic acid analysis in real time.

Figure 1:
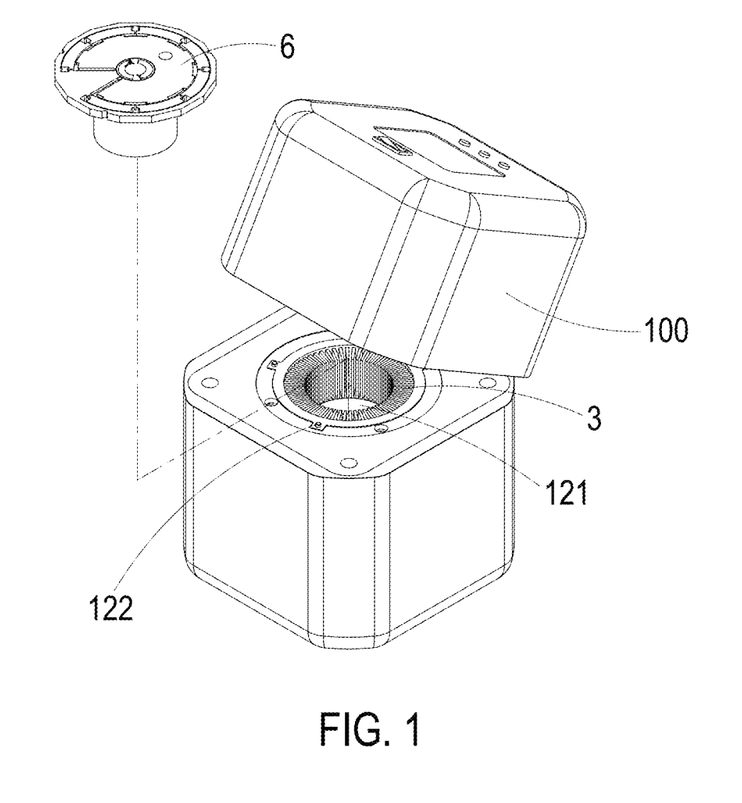
FIGS. 1-3 show schematic views of the nucleic acid analysis apparatus according to the embodiment of the present invention.
Figure 2:
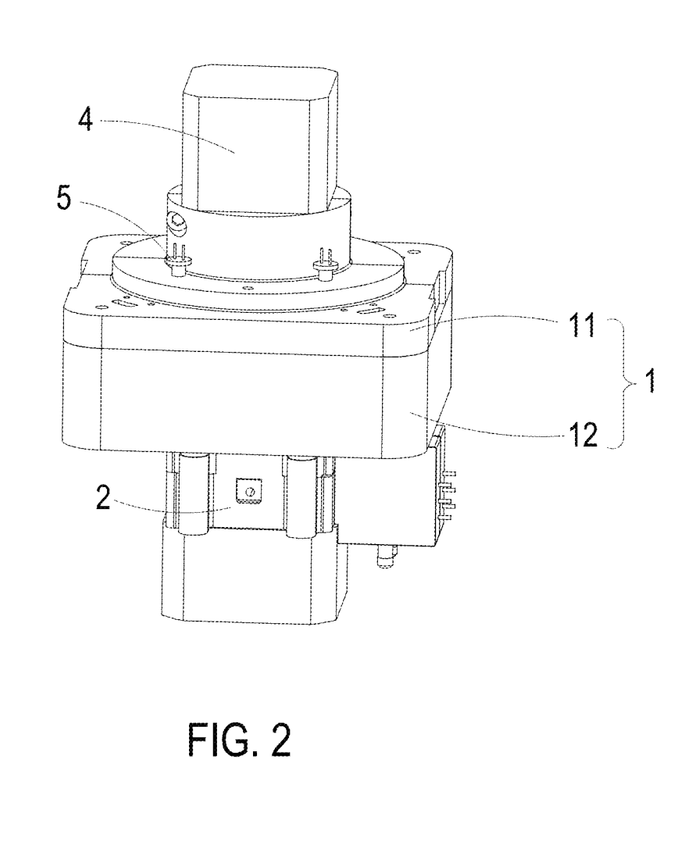
Figure 3:
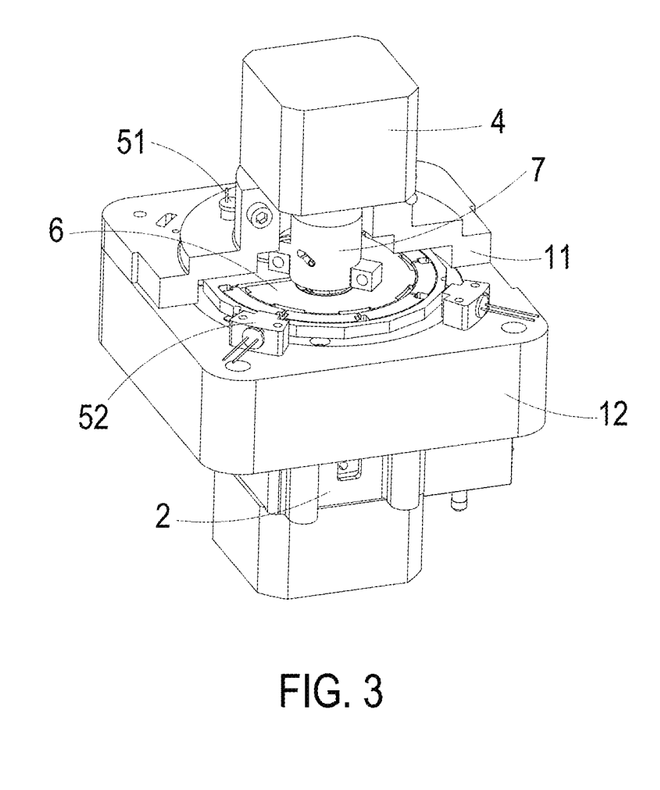

FIGS. 1-3 show schematic views of the nucleic acid analysis apparatus according to the embodiment of the present invention, wherein the nucleic acid analysis apparatus in FIG. 1 is opened and the cartridge is moved out of the nucleic acid analysis apparatus, and the outer housing of the nucleic acid analysis apparatus is removed in FIG. 2 and parts of the top chamber of the nucleic acid analysis apparatus is further removed in FIG. 3 to show the internal structures of the nucleic acid analysis apparatus. As shown in FIGS. 1 to 3, the nucleic acid analysis apparatus 100 includes a chamber 1, a fluid delivery unit 2, a thermal unit 3, a rotational driven unit 4, and at least one optical unit 5. The chamber 1 is able to be opened for mounting a cartridge 6 therein. The fluid delivery unit 2 is connected with the chamber 1 and adapted to transport reagents within the cartridge 6 for sample purification and/or nucleic acid extraction. The thermal unit 3 is disposed in the chamber 1 and adapted to provide a predefined temperature for nucleic acid amplification. The rotational driven unit 4 is connected with the chamber 1 and includes a motion control unit 7, wherein the motion control unit 7 is capable of pressing the cartridge 6 during sample purification and/or nucleic acid extraction and rotating the cartridge 6 with a predefined program during nucleic acid amplification and/or detection. The at least one optical unit 5 is disposed on the chamber 1 and includes plural optical components for detection, such as nucleic acid detection or sample reaction detection.

In an embodiment, the chamber 1 includes a top chamber 11 and a bottom chamber 12. The top chamber 11 and the bottom chamber 12 are connected through a hinge, but not limited thereto. The bottom chamber 12 has a cavity 121 specifically designed for mounting the cartridge 6 therein. The top chamber 11 can be opened, so that the cartridge 6 is able to be placed into the cavity 121 of the bottom chamber 12. When the top chamber 11 is closed, a confined space is formed in the chamber 1.

In an embodiment, the shape of the chamber 1 could be but not limited as cylindrical, spherical, cubic, conical or olivary, and the chamber 1 could be made but not limited by metal, ceramic, polymer, polymer compound, wood, glass, or other materials.

The bottom chamber 12 is connected with the fluid delivery unit 2. After the cartridge 6 is mounted in the bottom chamber 12, the cartridge 6 will be forced to tightly contact the fluid delivery unit 2 without leakage.

Figure 4:
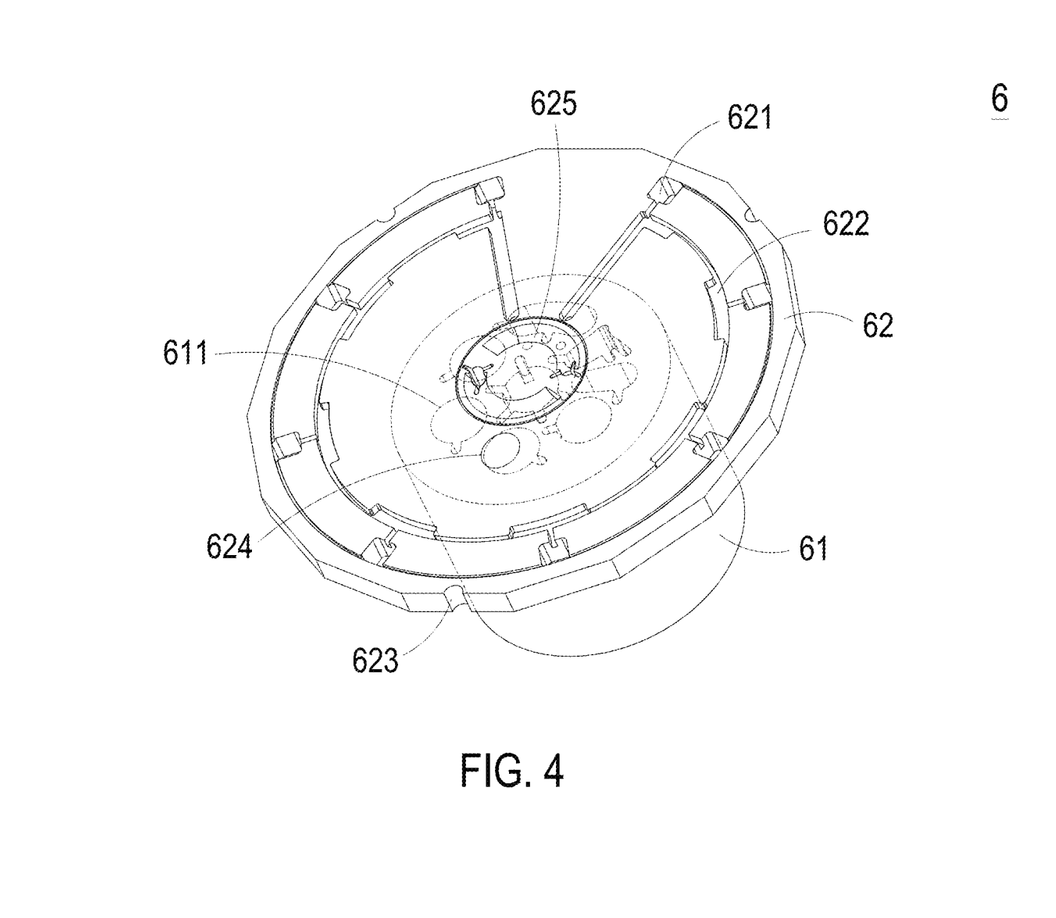
FIGS. 4 and 5 show different views of the cartridge.
Figure 5:
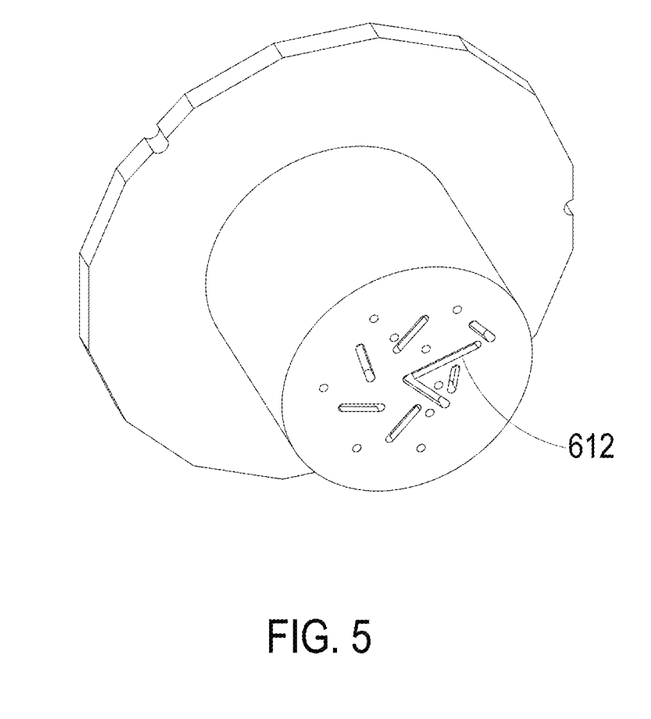

FIGS. 4 and 5 show different views of the cartridge. As shown in FIGS. 4 and 5, the cartridge 6 includes a cartridge body 61 and a reaction chip 62, and the reaction chip 62 is disposed on one side of the cartridge body 61, such as the top of the cartridge body 61. The reaction chip 62 is a planar fluidic chip, and includes plural detection wells 621 and at least one microchannel 622 connected with the detection wells 621. In an embodiment, the detection wells 621 include reagents for nucleic acid amplification and/or detection. For example, the detection wells 621 may be coated with reagents for nucleic acid amplification and/or detection, such as reagents containing different fluorescent dyes.

The number of the detection wells 621 is not limited, and may be up to 40 or even more, and the apparatus could perform multiplexing nucleic acid analysis. In an embodiment, the shape of the reaction chip 62 is substantially a regular polygon, so that the reaction chip 62 has plural planar side surfaces to be in line with the optical unit 5 to facilitate light focusing. Certainly, the shape of the reaction chip 62 is not limited to the regular polygon and it may also be circular or other shape, since the light could be focused on the sample in the detection well 621 by the arrangement of optical components of the optical unit 5.

In an embodiment, the reaction chip 62 further includes at least one alignment slot 623, and the bottom chamber 12 further includes at least one positioning component 122 (as shown in FIG. 1). For example, the positioning component 122 includes a positioning pin. When the cartridge 6 is placed into the cavity 121 of the bottom chamber 12, the alignment slot 623 of the cartridge 6 is aligned with the positioning component 122 of the bottom chamber 12, which helps an easy cartridge loading, and accordingly, the cartridge 6 may be self-aligned with the fluid delivery unit 2, and each optical unit 5 is in line with one of the detection wells 621. In an embodiment, each of the detection wells 621 has at least one planar surface. For example, the detection well 621 may be rectangular-shaped and have one planar surface in line with an optical detector of the optical unit 5 during nucleic acid detection.

The cartridge body 61 includes plural chambers 611 used to store reagents for sample purification and/or nucleic acid extraction. The cartridge body 61 also includes plural channels connected with the chambers 611 for fluid delivery. In an embodiment, the cartridge body 61 is but not limited to a cylindrical body. The cartridge body 61 further includes plural openings 612 at the bottom surface of the cartridge body 61, and the openings 612 are communicated with the chambers 611 through the channels. The shape of the openings 612 may be but not limited to circular, linear or other regular or irregular shape.

The reaction chip 62 further includes at least one sample loading hole 624 at the top surface of the reaction chip 62, and the sample loading hole 624 aligns and communicates with at least one chamber 611 of the cartridge body 61 for adding sample into the cartridge 6.

Figure 6:
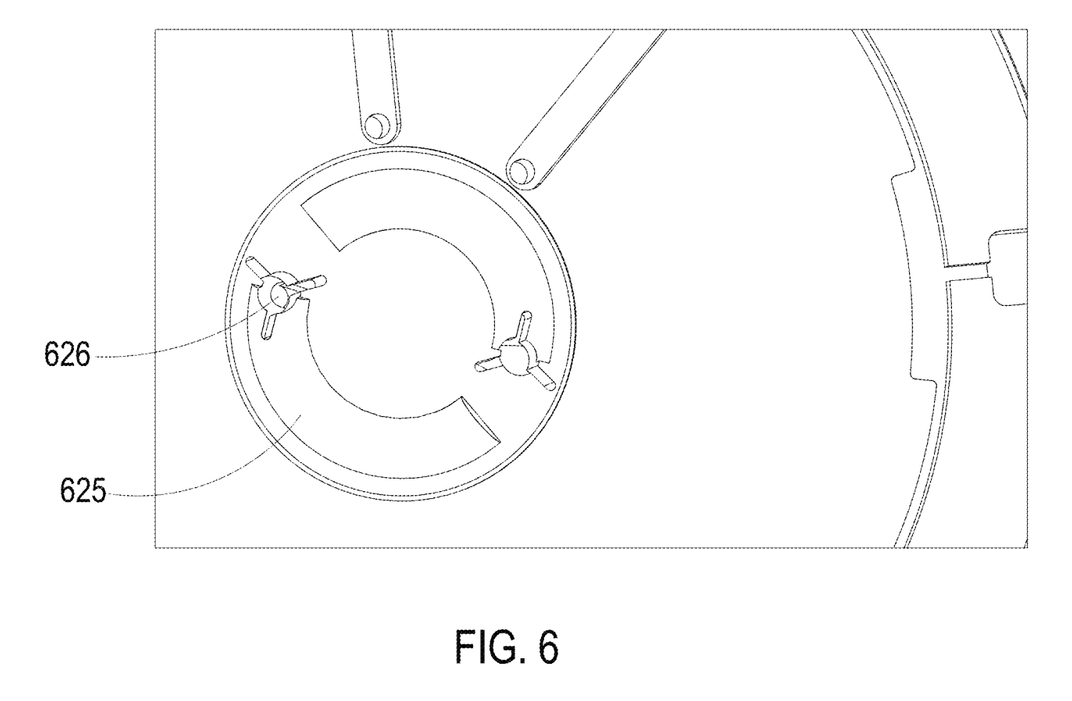
FIG. 6 shows a partial enlargement of the reaction chip.
Figure 7A:
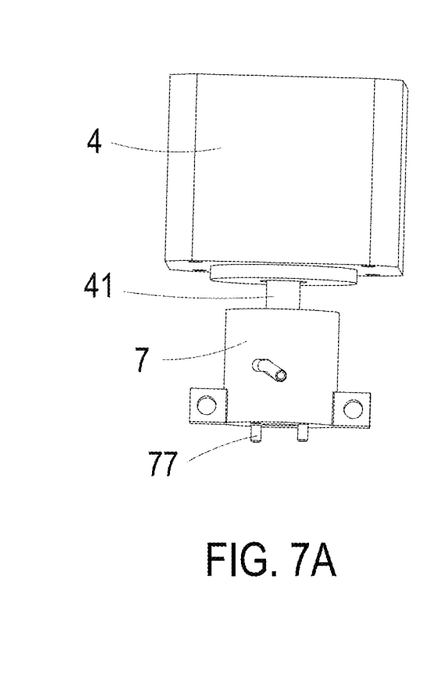
FIGS. 7A and 7B show different views of the rotational driven unit.
Figure 7B:
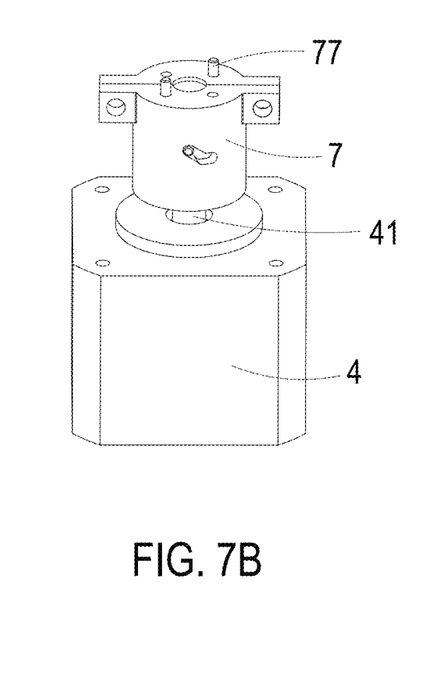

FIG. 6 shows a partial enlargement of the reaction chip. As shown in FIG. 4 and FIG. 6, the reaction chip 62 further includes at least one trench 625 at the top surface of the reaction chip 62, wherein the at least one trench 625 matches at least one clamping component 77 (as shown in FIGS. 7A and 7B) of the rotational driven unit 4, and the clamping component 77 is able to move in the trench 625. In an embodiment, the reaction chip 62 includes two trenches 625, and the rotational driven unit 4 includes two clamping components 77 as well, but the number of each of the trenches 625 and the clamping components 77 is not limited to two. The trenches 625 are arc-shaped and symmetrically disposed in the center of the reaction chip 62. Each trench 625 further includes a recess structure 626 matching the protruded clamping component 77 at one end of the trench 625, and the clamping component 77 can cowork with the recess structure 626 so as to clamp the cartridge 6. In an embodiment, the recess structure 626 is a hole but not limited thereto, and the diameter of the recess structure 626 is substantially the same as or slightly smaller than that of the clamping component 77, so as to tightly hold the clamping component 77 therein.

During the operation, once the sample is loaded, the cartridge 6 is placed into the nucleic acid analysis apparatus 100 and the flow processing is carried out by the fluid delivery unit 2. The fluid delivery unit 2 works concurrently with the cartridge 6 to carry out sample purification, nucleic acid extraction and fluid delivery so as to have a fully automatic device. The fluid delivery could be realized by pneumatic, vacuum, plunger, chamber deformation, thermal-induced expansion, acoustics, centrifugal force or other methods as long as the sample processing is completed within the cartridge body 61.

In an embodiment, the flow is driven pneumatically through microchannels and holes. For example, the fluid delivery unit 2 is similar to the integrated fluidic module of U.S. patent application Ser. No. 15/217,511 filed on Jul. 22, 2016 and issued as U.S. Pat. No. 10,124,335 on Nov. 13, 2018, which claims the priority to Singapore Patent Application No. 10201605723Y filed on Jul. 13, 2016, by the applicant of the present invention, the entire contents of which are incorporated herein by reference and are not redundantly described here. In brief, the fluid delivery unit 2 of the present invention includes the fluid manifold, the valve stator, the valve rotor, the valve housing and the fluid sources as disclosed in U.S. patent application Ser. No. 15/217,511. The fluid manifold includes plural microchannels for connecting with the chambers 611 of the cartridge 6 through the bottom openings 612. By the alignments of the through holes and/or grooves of the valve stator and the valve rotor, multi-way fluid path switching is realized when the valve rotor is rotated to different positions, so as to regulate the fluid operations in the cartridge 6. Thereby, the reagents stored within the cartridge 6 are able to be transported to desired locations through pneumatic force from pumps of the fluid delivery unit 2, so as to automatically perform the sample purification and the nucleic acid extraction. Certainly, the fluid delivery unit 2 is not limited to the above-mentioned design, and can be any other type as long as it is able to realize multiple fluid delivery and multi-way fluid path switching in the cartridge 6.

The rotational driven unit 4 is mounted on the top chamber 11. The rotational driven unit 4 is but not limited to a motor, and it may also be solenoid, manual operation, spring, clockwork or other components, and is able to clamp and rotate the cartridge 6 at predefined angles and speeds and pass each detection well 621 in alignment with each optical unit 5 sequentially. In an embodiment, the rotational driven unit 4 includes a step motor, which is able to drive the rotation of the cartridge 6 in different patterns. The rotational driven unit 4 further includes a motion control unit 7, which is adapted to clamp and rotate the cartridge 6 during nucleic acid amplification and detection, and also provide good sealing between the cartridge 6 and the fluid delivery unit 2 during sample purification and nucleic acid extraction.

Figure 8A:
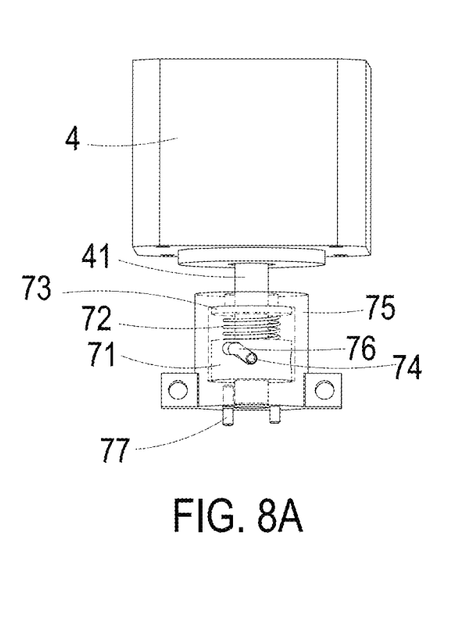
FIGS. 8A and 8B show the inner structures of the motion control unit in different positions.
Figure 8B:
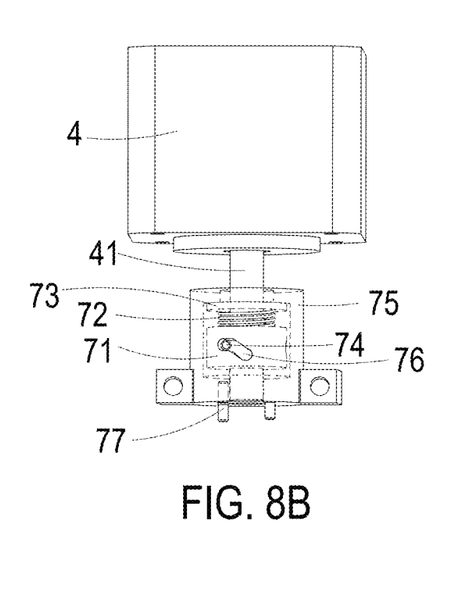

FIGS. 7A and 7B show different views of the rotational driven unit. FIGS. 8A and 8B show the inner structures of the motion control unit in different positions. As shown in FIGS. 7A to 8B, the rotational driven unit 4 includes a driven shaft 41, and the motion control unit 7 is mounted on the driven shaft 41. The motion control unit 7 includes a fixed part 71, a spring 72, a flat plate 73, at least one protrusion 74, a sliding shell 75 and at least one groove 76. The fixed part 71 is mounted on the driven shaft 41 at a fixed position and covered by the sliding shell 75. The sliding shell 75 provides an inner space for accommodating the fixed part 71, the spring 72, and the flat plate 73 therein. The spring 72 is sandwiched between the fixed part 71 and the flat plate 73. The fixed part 71 is against the inner bottom wall of the sliding shell 75, and the flat plate 73 is against the inner top wall of the sliding shell 75. The groove 76 is a through hole formed on the sliding shell 75, and is shaped like a playground slide having a plateau at top and a downward ramp. The protrusion 74 is protruded out of the fixed part 71 and inserted into the groove 76. Due to the cowork of the protrusion 74 on the fixed part 71 and the groove 76 on the sliding shell 75, the motion of the sliding shell 75 is restrained within a controllable range. Once released, the sliding shell 75 could return to its original position due to the resilience of the spring 72.

In some embodiments, the protrusion 74 and the groove 76 may be some other similar structures that could cowork with each other. The positions of the protrusion 74 and the groove 76 may also be interchanged. In an embodiment, the protrusion 74 is formed on the sliding shell 75 and the groove 76 is formed on the fixed part 71.

During the operation of the rotational driven unit 4, the fixed part 71 can rotate with the driven shaft 41. Since the protrusion 74 on the fixed part 71 is inserted into the groove 76 on the sliding shell 75, the rotation of the fixed part 71 also drives the rotation of the sliding shell 75. If the rotation of the sliding shell 75 is constrained by an external force and cannot rotate in some conditions, the further motor rotation of the rotational driven unit 4 will drive the driven shaft 41 and the fixed part 71 keep moving forwardly. As a result, the sliding shell 75 changes its position axially along the driven shaft 41, due to the cowork of the protrusion 74 on the fixed part 71 and the groove 76 on the sliding shell 75.

The motion control unit 7 further includes at least one clamping component 77 protruded out of the bottom surface of the sliding shell 75. In an embodiment, the motion control unit 7 includes two clamping components 77, and the clamping components 77 are dowel pins, but not limited thereto. The clamping components 77 match the trenches 625 on the reaction chip 62 of the cartridge 6.

Figure 9A:
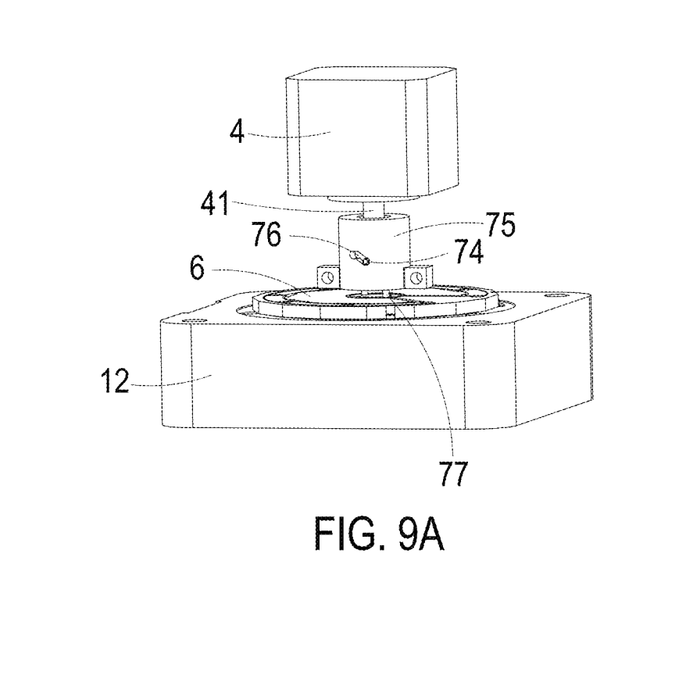
FIGS. 9A and 9B show different views of the rotational driven unit, the cartridge and the bottom chamber when the motion control unit is at the higher position.
Figure 9B:
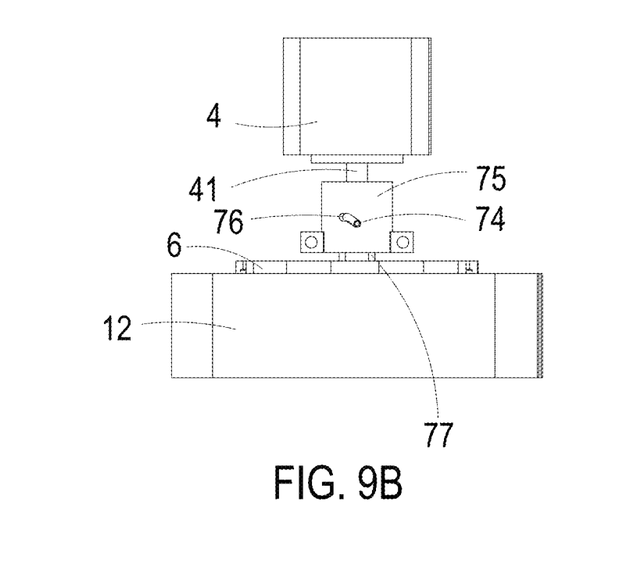
Figure 10A:
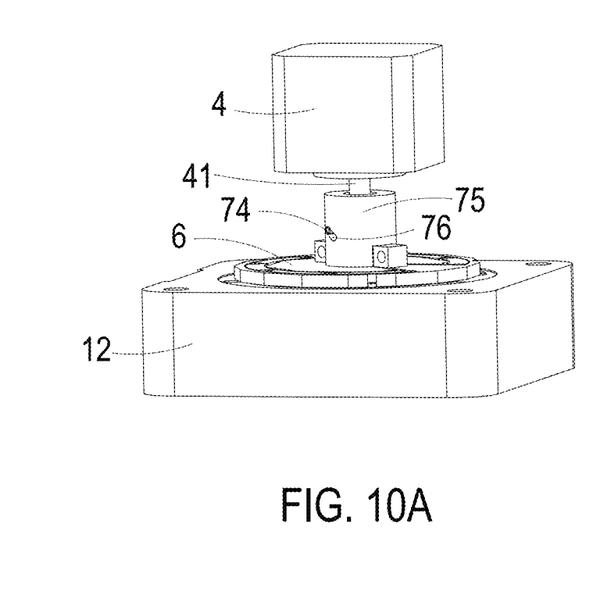
FIGS. 10A and 10B show different views of the rotational driven unit, the cartridge and the bottom chamber when the motion control unit is at the lower position.
Figure 10B:
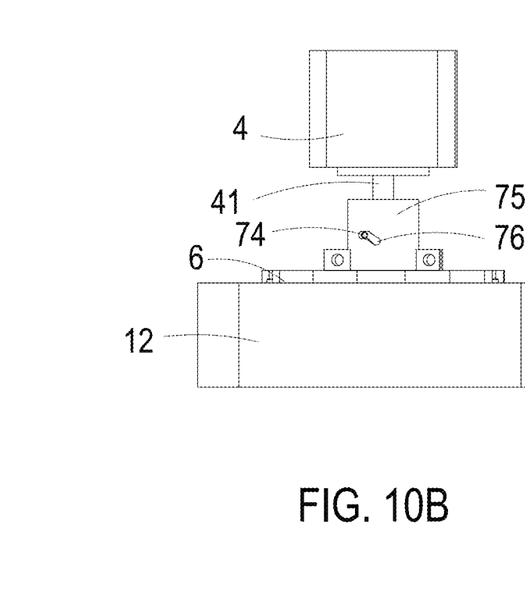

FIGS. 9A and 9B show different views of the rotational driven unit, the cartridge and the bottom chamber when the motion control unit is at the higher position, and FIGS. 10A and 10B show different views of the rotational driven unit, the cartridge and the bottom chamber when the motion control unit is at the lower position. When the cartridge 6 is loaded into the bottom chamber 12 and the top chamber 11 is closed, the terminal of the clamping component 77 on the sliding shell 75 is just located in the trench 625 on the cartridge 6, and the protrusion 74 on the fixed part 71 is at the lower end of the groove 76 on the sliding shell 75, as shown in FIGS. 8A, 9A and 9B, wherein a small gap exists between the bottom surface of the sliding shell 75 and the top surface of the cartridge 6. With the rotation of the driven shaft 41, the clamping component 77 on the sliding shell 75 also rotates until it is constrained by the end of the trench 625. As the position of the cartridge 6 is constrained by the positioning component 122, the further rotation of the sliding shell 75 is blocked, and thus, the sliding shell 75 slides downwardly to its lower position and the protrusion 74 on the fixed part 71 moves to the top plateau of the groove 76 on the sliding shell 75, as shown in FIGS. 8B, 10A and 10B. Meanwhile, the clamping component 77 inserts downwardly into the recess structure 626 at the end of the trench 625 on the cartridge 6 and therefore clamps the cartridge 6. At the same time, the downward sliding shell 75 also applies a force on the cartridge 6 and presses it to have a superior contact to the fluid deliver unit 2, allowing a smooth fluid processing.

After the fluid processing is completed and the purified sample is delivered to the detection wells 621 on the reaction chip 62 of the cartridge 6, the cartridge 6 needs to be lifted up and rotate during the detection. At this time, the driven shaft 41 rotates reversely and the protrusion 74 also rotates reversely with the driven shaft 41. As the cartridge 6 is constrained by the positioning component 122 at this moment, the clamping component 77 as well as the sliding shell 75 cannot rotate with the driven shaft 41 except the fixed part 71 and the protrusion 74. Once the protrusion 74 on the fixed part 71 leaves the plateau of the groove 76, the resilience of the spring 72 will push the sliding shell 75 upwardly to its original position and therefore lift the cartridge 6 above the positioning component 122 and away from the fluid deliver unit 2. Thus, the friction between the interfaces is minimized and the cartridge 6 could freely rotate within the chamber 1 during the nucleic acid amplification and/or detection. Further following the rotation of the driven shaft 41, the cartridge 6 is clamped and rotated with the predefined programs to align the detection wells 621 with each optical unit 5 sequentially for nucleic acid detection.

Figure 11:
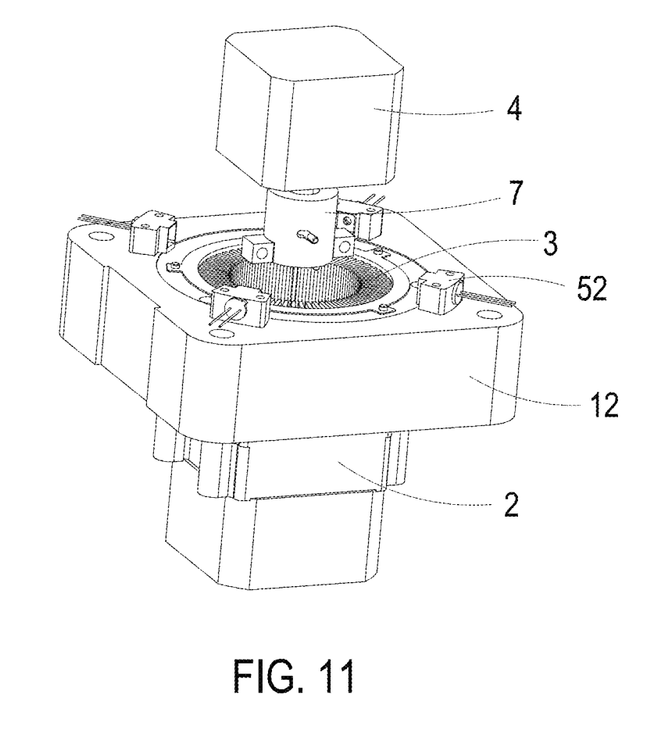
FIG. 11 shows a schematic view of the nucleic acid analysis apparatus wherein the top chamber is removed to expose the thermal unit.

FIG. 11 shows a schematic view of the nucleic acid analysis apparatus wherein the top chamber is removed to expose the thermal unit. As shown in FIGS. 1 and 11, the thermal unit 3 is disposed in the cavity of the bottom chamber 12 and may include a heater and plural heat sinks arranged as a circle. When the cartridge 6 is loaded into the bottom chamber 12, the thermal unit 3 surrounds the cartridge body 61 and carries the reaction chip 62 thereon. Therefore, the reaction chip 62 is in direct contact with the thermal unit 3 and could be heated by contact heating, which has superior heating efficiency and reduced heating time.

The nucleic acid analysis apparatus 100 is designed to amplify nucleic acid based on isothermal method and therefore only a constant temperature instead of thermal cycling among three different temperature zones is needed. As a result, the thermal unit 3 is significantly simplified. In addition, the chamber 1 of the nucleic acid analysis apparatus 100 is designed with superior thermal insulation and therefore the inner temperature is easily maintained. Once the chamber 1 is in a uniform temperature environment, heat loss from the detection wells 621 and sample towards the environment could be minimized. At the amplification and/or detection processes, the whole closed chamber 1 and the sample at each detection well 621 are substantially in the same temperature, regardless the cartridge 6 is in motion or in stationary.

The thermal unit 3 provides the required temperature within the chamber 1 during the operation, wherein the temperature control is independent of the number and shape of detection wells 621. In an embodiment, the thermal unit 3 further includes a temperature sensor to control the accuracy of the temperature.

In an embodiment, the nucleic acid analysis apparatus 100 includes multiple optical units 5. The optical unit 5 has optical components such as light source, lens, filter and optical detector to realize the optical detection so that the sample could be detected in real time during the nucleic acid amplification. As shown in FIG. 3, the optical unit 5 includes at least one light source 51 and at least one optical detector 52. The light source 51, such as LED, and the optical detector 52 are both embedded within the top chamber 11. During the operation, each light source 51 aligns to one of the detection wells 621 of the cartridge 6 in order to offer effective illumination for detection. Once the cartridge 6 is clamped, the optical detector 52, such as photodiode, is in line with one of the detection wells 621 on the cartridge 6 and therefore the results of nucleic acid analysis are interpreted. The rotation of the cartridge 6 allows each detection well 621 to pass through different optical units 5 sequentially. In an embodiment, each optical unit 5 could offer a unique wavelength of illumination so as to provide different colors for fluorescent based detection, and thus, the nucleic acid analysis apparatus 100 can detect multiple targets simultaneously and realize multiplexing detection.

In an embodiment, the nucleic acid analysis apparatus 100 includes a controller, which controls the operations of the fluid delivery unit 2, the thermal unit 3, the rotational driven unit 4 and the optical unit 5.

By utilizing the isothermal based amplification, the thermal unit 3 is significantly simplified, and thus, the nucleic acid analysis apparatus 100 can be compact designed and is even smaller than a common teacup. In an embodiment, the nucleic acid analysis apparatus 100 has a height ranged between 100 mm and 120 mm and a width ranged between 80 mm and 100 mm. Since the nucleic acid analysis apparatus 100 is cup sized, it is portable and suitable for POC diagnostics.

The nucleic acid analysis apparatus 100 is designed for isothermal based amplification, and thus can be used to perform all isothermal amplification methods, such as nucleic acid sequence-based amplification (NASBA), strand displacement amplification (SDA), helicase-dependent amplification (HDA), loop-mediated isothermal amplification (LAMP), recombinase polymerase amplification (RPA) and nicking enzyme amplification reaction (NEAR).

Figure 12:
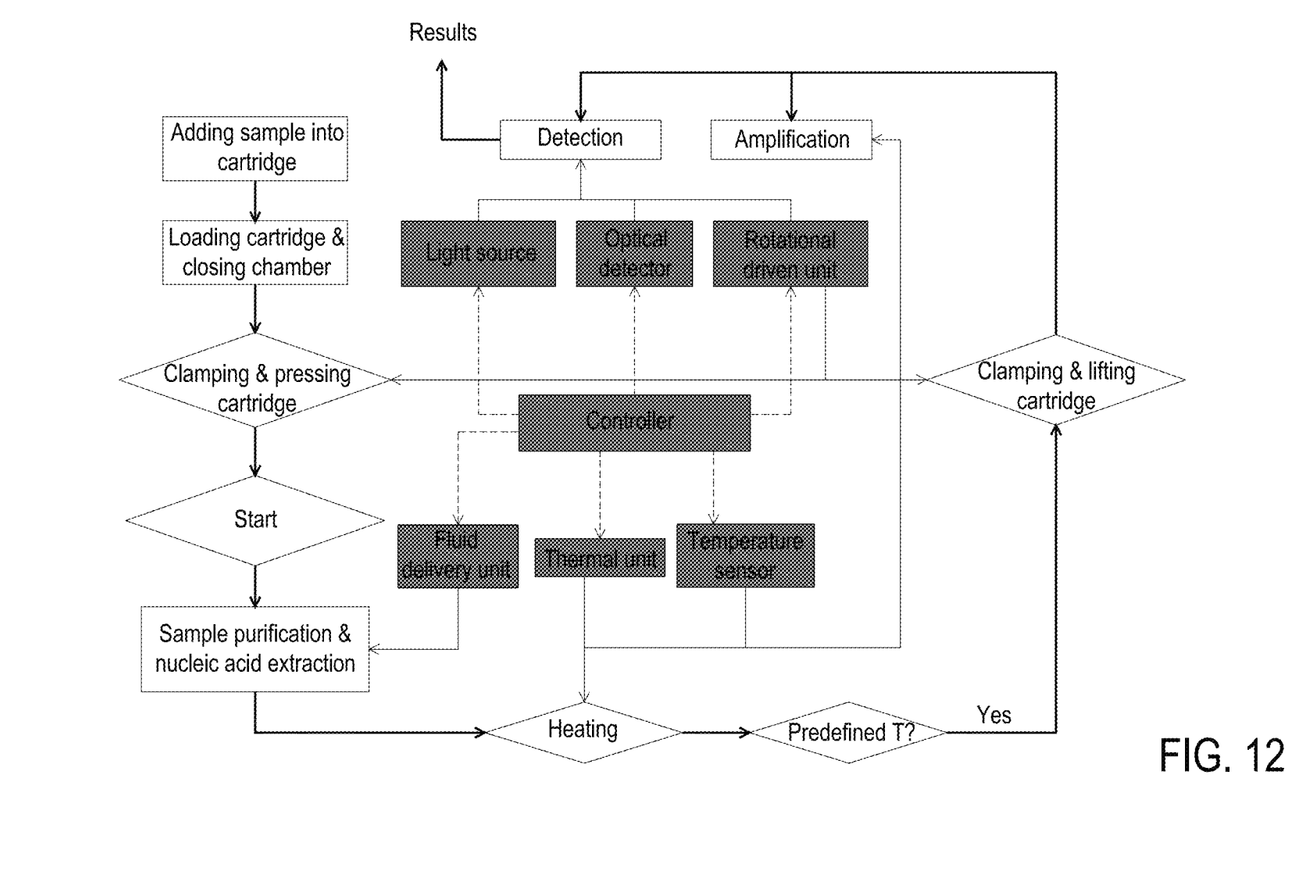
FIG. 12 shows the flow chart of the operation of the nucleic acid analysis apparatus.

FIG. 12 shows the flow chart of the operation of the nucleic acid analysis apparatus. The thick arrows indicate the procedure of the operation. The hollow boxes indicate several main actions, and the hollow diamonds show main steps to complete the operation. The gray boxes indicate core hardware components of the apparatus. Communications from the controller to the hardware components are illustrated by dashed arrows and the responses of the hardware components to yield predefined functionalities are illustrated by thin arrows. The operation procedures of the nucleic acid analysis apparatus 100 are described as follows with reference to FIGS. 1 to 12.

In the first step, manual operations are performed. The top chamber 11 of the nucleic acid analysis apparatus 100 is opened. The sample is added to the cartridge 6 through the sample loading hole 624 on the reaction chip 62, wherein the reagents for the sample purification and the nucleic acid extraction are preloaded in the chambers 611 of the cartridge body 61. After the sample is added into the cartridge 6, the cartridge 6 is loaded into the bottom chamber 12 and the top chamber 11 is closed. Once the cartridge 6 is placed into the cavity 121 of the bottom chamber 12, the positioning component 122 on the bottom chamber 12 helps the cartridge 6 self-aligned with the fluid delivery unit 2. The rotational driven unit 4 further drives the motion control unit 7 to clamp and press the cartridge 6, so that the cartridge 6 is forced to contact the fluid delivery unit 2 tightly. Then the sample processing is started.

In the second step, the sample purification and the nucleic acid extraction are performed. In this step, sample processing is carried out within the cartridge 6 and the reagents, such as biochemical buffers, are transported to each desired locations through the assistance of the fluid delivery unit 2. After the sample purification and the nucleic acid extraction are completed, the sample with extracted nucleic acid is dispensed to the detection wells 621 of the cartridge 6 for following nucleic acid amplification and/or detection.

In the third step, the chamber 1 is heated by the thermal unit 3 to reach the predefined temperature, wherein the sample in the detection wells 621 is heated by contact heating to have a rapid temperature rising. In addition, the temperature sensor is used to monitor the sample temperature.

In the fourth step, the nucleic acid amplification and the nucleic acid detection are performed. When the sample temperature reaches a predefined value, the cartridge 6 is clamped and lifted by the motion control unit 7, and the isothermal based amplification is started. Meanwhile, the thermal unit 3 is still in operation to maintain the temperature. Once the cartridge 6 is lifted, it is able to rotate within the chamber 1, which is actuated by the rotational driven unit 4. The cartridge 6 is able to rotate with a certain angle so that each detection well 621 aligns with the optical unit 5 and stops for a short period (200 ms, for example) for detection. Thereby, each detection well 621 is able to pass through a series of light sources 51 with different colors and the emitted lights are able to be detected with the optical detectors 52, such as photodiode.

After the detection is completed, the detection results may be sent to cloud or digital devices, such as PC, tablet or smart phone, through USB or wireless. The chamber 1 is opened and the cartridge 6 is discarded.

In the above embodiments, the cartridge 6 is illustrated as one-in-one cartridge, which means one sample per detection. However, in another embodiment, the cartridge 6 may be X-in-one cartridge, which means X samples per detection. For example, the reaction chip 62 could includes plural sample loading holes 624 for adding plural different samples into the same cartridge 6 to have flexible throughput (1~X), without increasing hardware cost.

In conclusion, the embodiment of the present invention provides an all-in-one nucleic acid analysis apparatus with isothermal based amplification, which integrates the fluid delivery unit, the thermal unit, the rotational driven unit and the optical unit on one single device, so that the processes of sample purification, nucleic acid extraction, nucleic acid amplification and nucleic acid detection can be performed on the all-in-one apparatus to realize nucleic acid analysis in real time. Therefore, the nucleic acid analysis apparatus provides an easy and fast nucleic acid analysis. Moreover, the cartridge pressing, cartridge clamping, cartridge lifting and cartridge rotating can be all realized by the rotational driven unit only, so the nucleic acid analysis apparatus has extremely simplified structural design with minimized components. The downward force provided by the rotational driven unit enhances the sealing between the cartridge and the fluid delivery unit, so as to provide a smooth fluid processing. The contact heating of the thermal unit further improves the heating efficiency. Further, due to the arrangements of multiple detection wells and multiple optical units, both multiplexing nucleic acid analysis and multiple color multiplexing detection are achieved. In addition, since the thermal unit is significantly simplified, the nucleic acid analysis apparatus can be compact designed, so it is portable and suitable for POC diagnostics. Also, the cost for nucleic acid analysis is also reduced. Besides, the nucleic acid analysis apparatus has acceptable sensitivity and specificity, and flexible throughput as well.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A nucleic acid analysis apparatus with isothermal based amplification, comprising:
    a chamber comprising a cartridge mounted therein;
    a fluid delivery unit connected with the chamber and adapted to transport reagents within the cartridge for sample purification and/or nucleic acid extraction, wherein the fluid delivery unit comprises a plurality of microchannels for connecting with the cartridge and a pump adapted to provide pneumatic force to transport the reagents stored within the cartridge;
    a thermal unit disposed in the chamber and comprising a heater to provide a predefined temperature for nucleic acid amplification;
    a rotational driven unit connected with the chamber and comprising a motor, a driven shaft, and a motion control unit mounted on the driven shaft, wherein the motion control unit comprises a sliding shell and at least one clamping pin protruded out of a bottom surface of the sliding shell, wherein the driven shaft drives the rotation of the clamping pin to clamp and rotate the cartridge, and drives the sliding shell to move downwardly or upwardly to push down or lift up the cartridge, so that the motion control unit is capable of pressing the cartridge during sample purification and/or nucleic acid extraction and rotating the cartridge with a predefined program during nucleic acid amplification and/or detection; and
    at least one optical unit disposed on the chamber and comprising at least one light source and at least one optical detector for detection.

2. The nucleic acid analysis apparatus according to claim 1, wherein the chamber is able to be opened and comprises a top chamber and a bottom chamber.

3. The nucleic acid analysis apparatus according to claim 2, wherein the cartridge is mounted in a cavity of the bottom chamber.

4. The nucleic acid analysis apparatus according to claim 1, wherein a rotation of the driven shaft drives the sliding shell to move downwardly and push the cartridge in contact with the fluid delivery unit.

5. The nucleic acid analysis apparatus according to claim 4, wherein the cartridge comprises at least one trench and at least one recess structure matching the clamping pin at one end of the trench, and when the sliding shell moves downwardly, the clamping pin works in conjunction with the recess structure so as to clamp the cartridge.

6. The nucleic acid analysis apparatus according to claim 5, wherein a reverse rotation of the driven shaft drives the sliding shell to move upwardly and lift the cartridge away from the fluid delivery unit.

7. The nucleic acid analysis apparatus according to claim 4, wherein the motion control unit comprises a fixed part and at least one protrusion, the fixed part is mounted on the driven shaft at a fixed position, and the protrusion is protruded out of the fixed part and inserted into a groove on the sliding shell.

8. The nucleic acid analysis apparatus according to claim 7, wherein the motion control unit comprises a spring disposed between the fixed part and the sliding shell.

9. The nucleic acid analysis apparatus according to claim 1, wherein the cartridge comprises a reaction chip and a cartridge body, and the reaction chip is disposed on one side of the cartridge body.

10. The nucleic acid analysis apparatus according to claim 9, wherein the reaction chip is a planar fluidic chip and comprises a plurality of detection wells and at least one microchannel connected with the detection wells.

11. The nucleic acid analysis apparatus according to claim 10, wherein each of the detection wells has at least one planar surface.

12. The nucleic acid analysis apparatus according to claim 9, wherein the shape of the reaction chip is substantially a regular polygon.

13. The nucleic acid analysis apparatus according to claim 9, wherein the chamber further comprises at least one positioning pin, and the reaction chip comprises at least one alignment slot capable of being aligned with the at least one positioning pin on the chamber.

14. The nucleic acid analysis apparatus according to claim 9, wherein the cartridge body comprises a plurality of chambers used to store reagents for sample purification and nucleic acid extraction.

15. The nucleic acid analysis apparatus according to claim 9, wherein the reaction chip further comprises at least one sample loading hole at a top surface of the reaction chip for adding sample into the cartridge.

16. The nucleic acid analysis apparatus according to claim 9, wherein the thermal unit surrounds the cartridge body and carries the reaction chip thereon to provide contact heating.

17. The nucleic acid analysis apparatus according to claim 1, wherein the rotational driven unit comprises a step motor to rotate the cartridge at a predefined angle.

18. The nucleic acid analysis apparatus according to claim 1, wherein the nucleic acid analysis apparatus comprises multiple optical units, and each optical unit offers a unique wavelength of illumination to detect multiple targets.

* * * * *